United States Patent
Calapez De Albuquerque Veloso et al.

(10) Patent No.: US 11,000,240 B2
(45) Date of Patent: May 11, 2021

(54) SYSTEM AND METHOD OF POSITRON EMISSION TOMOGRAPHY WITH TWO AXES OF ROTATION

(71) Applicant: UNIVERSIDADE DE AVEIRO, Aveiro (PT)

(72) Inventors: João Filipe Calapez De Albuquerque Veloso, Ilhavo (PT); Ismael Filipe Correia De Castro, Santa Maria da Feira (PT); Luís Miguel Da Conceição Moutinho, Aveiro (PT); Lara Filipa Das Neves Dias Carramate, Mealhada (PT); Pedro Manuel Mendes Correia, Gafanha da Encarção (PT); Ana Luísa Monteiro Da Silva, Aveiro (PT)

(73) Assignee: UNIVERSIDADE DE AVEIRO, Aveiro (PT)

( * ) Notice: Subject to any disclaimer, the term of this patent is extended or adjusted under 35 U.S.C. 154(b) by 730 days.

(21) Appl. No.: 15/558,778

(22) PCT Filed: Mar. 16, 2016

(86) PCT No.: PCT/IB2016/051487
§ 371 (c)(1),
(2) Date: Sep. 15, 2017

(87) PCT Pub. No.: WO2016/147130
PCT Pub. Date: Sep. 22, 2016

(65) Prior Publication Data
US 2018/0070893 A1    Mar. 15, 2018

(30) Foreign Application Priority Data
Mar. 16, 2015   (PT) .......................... 108284

(51) Int. Cl.
| | | |
|---|---|---|
| *A61B 6/03* | (2006.01) | |
| *G01T 1/29* | (2006.01) | |
| (Continued) | | |

(52) U.S. Cl.
CPC .............. *A61B 6/037* (2013.01); *A61B 6/508* (2013.01); *G01T 1/1648* (2013.01); *G01T 1/20* (2013.01); *G01T 1/2985* (2013.01)

(58) Field of Classification Search
CPC ....... A61B 6/037; A61B 6/508; G01T 1/2985; G01T 1/1648; G01T 1/20
See application file for complete search history.

(56) References Cited

U.S. PATENT DOCUMENTS

| | | | | |
|---|---|---|---|---|
| 5,262,648 A | * | 11/1993 | Stark ....................... | G01T 1/166 250/363.02 |
| 2006/0274880 A1 | * | 12/2006 | Oikawa .................... | A61B 6/02 378/21 |

(Continued)

OTHER PUBLICATIONS

Veloso et al. (some co-inventors but different inventive entity), EasyPET: A user friendly PET system for didactic purposes, Feb. 8, 2015 (archive.org retrieval date), Hands-on Science Network, pp. 226-230 (Year: 2015).*

(Continued)

*Primary Examiner* — David P Porta
*Assistant Examiner* — Jeremy S Valentiner
(74) *Attorney, Agent, or Firm* — Leason Ellis LLP

(57) ABSTRACT

System of positron emission tomography to obtain images of a subject, which comprehends: one first fixed axis of rotation; one second axis of rotation substantially parallel to the first axis, in which the second axis is rotatable around the first axis at a predefined distance; one element of support rotatably coupled to the second axis; one pair of scintillators fixed to the element of support, said pair being collinear and aligned along the same longitudinal axis; two photomulti- (Continued)

pliers, each optically coupled to one of the scintillators; in which the element of support has a free region between the pair of scintillators to receive the subject to be imaged.

20 Claims, 2 Drawing Sheets

(51) Int. Cl.
*G01T 1/20* (2006.01)
*A61B 6/00* (2006.01)
*G01T 1/164* (2006.01)

(56) References Cited

U.S. PATENT DOCUMENTS

| | | | |
|---|---|---|---|
| 2008/0103391 A1* | 5/2008 | Dos Santos Varela | A61B 6/037 600/436 |
| 2012/0267537 A1* | 10/2012 | Gagnon | G01T 1/2985 250/363.03 |

OTHER PUBLICATIONS

Veloso et al.—EasyPET accessed on WayBack Machine with Feb. 8, 2015 capture at URL: https://web.archive.org/web/20150208211415/http://hsci.info/Book_HSCI_2014_lowresA4.pdf on Jul. 1, 2020 (Year: 2015).*

JFCA Veloso et al, "EastPET. A Didactic PET System," Hands-on Science Education with and for Society, pp. 226-230. Feb. 8, 2015.

Pedro, R. et al, "The MiniPET: a didactic PET System," Journal of Instrumentation. p. 1-7. 2013.

Alavi, A. et al., "Implications of PET based Molecular Imaging on the Current and Future Practice of Medicine," Seminars in Nuclear Medicine, vol. XXXIV, No. 1, p. 56-59. Jan. 2004.

Bolle, E. et al., "Ax-PET: Anovel PET concept with G-APD readout," Nuclear Instruments and Methods in Physics Research A 695, p. 129-134. 2012.

Veloso, J. et al., "easyPET: a user friendly PET system for didactic purpose," 7th International Conference on New Developments in Photodetection. 2014.

JFCA Veloso et al, "EastPET. A Didactic PET System," 11th International Conference on Hands-on Science. Conference booklet, p. 21. Jul. 2014.

* cited by examiner

SYSTEM AND METHOD OF POSITRON EMISSION TOMOGRAPHY WITH TWO AXES OF ROTATION

CROSS-REFERENCE TO RELATED APPLICATIONS

This application is a U.S. National Stage Application under 35 U.S.C. § 371 of International Patent Application No. PCT/IB2016/051487, filed Mar. 16, 2016, which claims priority to Portugal Application No. 108284, filed Mar. 16, 2015, which are hereby incorporated by reference in their respective entireties.

TECHNICAL FIELD

The present description refers to nuclear instrumentation/imaging, in particular to a system of positron emission tomography, PET, which produces images of a subject containing positron emitting radioactive isotopes, more particularly a PET system that can have only two detector modules rotating around the object of PET, so as to cover a field of view similar to that of a complete ring of detectors.

BACKGROUND

Positron emission tomography (PET) is a powerful modality of medical imaging, capable of providing detailed functional information of physiological processes inside the body, which has been having a great impact in Oncology due to its capacity for disease detection, staging, evaluation of response to therapy and identification of recurrent disease [1]. The underlying principle of PET systems is the detection of gamma radiation emitted from a radioactive substance administered in the human body.

That substance contains radioisotopes of atoms existing in biological molecules and, therefore, it has affinity for certain metabolic or biochemical processes, allowing to study the function of a certain organ or evaluate the presence of disease, revealed by the excess concentration of that substance in specific locations of the body. For example, 18F-FDG (glucose labelled with Fluor radioisotope) is preferentially taken up by cancerous cells, since these have a glucose metabolic rate higher than normal cells. The molecules used in PET are labelled with positron emitting radioisotopes, which after annihilated with atomic electrons, emit two photons with energy of 511 keV, in the same line but with opposite directions.

PET systems detect and determine the spatial origin of these pairs of photons, by the intersection of the several lines of response generated from their emission. Even though 18-F-FDG is by far the tracer molecule most used in PET, new tracers are being developed for cancer diagnostics, detection of hypoxia and angiogenesis, thus an expansion of the role of this modality in the improvement of clinical diagnosis is foreseen.

A fundamental contribution for the development of new radiopharmaceuticals has been given by small dimension PET systems, which allow performing preclinical molecular imaging studies in small animals such as mice. These systems use a large number of detectors, normally disposed in the form of a ring and composed of scintillator crystals with individual cross-sectional area of few mm2.

Since the physical dimensions of the organs of small animals are of the order of mm, small dimension PET systems require a much better spatial resolution than human PET systems. While the spatial resolution of current human PET systems is of the order of 4-6 mm FWHM, systems for small animals aim for a sub-millimetric resolution.

The main factor that degrades the spatial resolution of small diameter PET systems has to do with the oblique penetration of 511 keV photons in the scintillator crystals, that results in a parallax error and subsequent uncertainty in the positioning of the lines of response, which is higher the further away from the centre of the field of view the positron source is.

To minimize that parallax error, different methods have been developed for determination of the depth of interaction (DoI) of the 511 keV photons in the scintillator crystals, methods which imply a higher complexity and cost of PET systems.

In order to build simpler PET systems with didactic purpose or prototypes for demonstration of new PET concepts, systems have been developed with only two detector modules or partial rings of detectors rotating around a central axis of rotation, so as to cover a field of view similar to that of a complete ring of detectors.

Document [2] discloses a didactic small dimension PET system, called MiniPET, with two detector modules, each composed of a matrix of 4×4 scintillator crystals coupled to a 16-channel photomultiplier tube (PMT). Through the action of motors, the modules can move along a circumference of variable radius in which, besides the face-to-face configuration with the diametrically opposed detectors moving together, one of the modules can rotate +/−90 degrees allowing to acquire lines of response away from the centre of rotation.

Document [3] discloses a system used to demonstrate a new concept of PET with application in high-resolution and high-sensitivity PET imaging, called AX-PET. In this demonstrative prototype two detector modules are used, in which one of them is fixed and the other can rotate +/−20 degrees around a central axis, acquiring lines of response not only crossing the centre but also in the periphery of the field of view. To obtain lines of response from all around the field of view, the objects are placed in a support which rotates up to 360 degrees. The combination of the two independent scans, of the rotative support and of one of the detector modules, allows simulating a ring with 18 modules.

The rotation movements of existing systems are however always performed around the same central axis. As a consequence, these systems continue to suffer degradation of the spatial resolution in peripheral zones of the field of view due to the parallax error, even if this is minimized by methods of correction through DOI determination (e.g., AX-PET).

Through a PET system and respective acquisition method with two axes of rotation, the present invention aims to reduce even further the number of detectors required for the obtention of a PET image, while at the same time it eliminates the parallax error and the need for determination of the DoI.

These facts are described in order to illustrate the technical problem solved by the embodiments of the present document.

References

[1] A. Alavi, J. W. Kung, H. Zhuang, Implications of PET based molecular imaging on the current and future practice of medicine. Seminars in Nuclear Medicine 56-69 2004

[2] R. Pedro et al., The MiniPET: a didactic PET system, Journal of Instrumentation 8 C03005 2013

[3] E. Bolle et al., AX-PET: A novel PET concept with G-APD readout, Nuclear Instruments and Methods in Physics Research A 695 129-134 2012

SUMMARY

The present description refers to nuclear instrumentation/imaging, in particular to a system of positron emission tomography, PET, which produces images of a subject containing positron emitting radioactive isotopes, more particularly a PET system that can have only two detector modules rotating around the object of PET, so as to cover a field of view similar to that of a complete ring of detectors.

A subject of positron emission tomography, PET, includes unanimated objects and living beings, namely animals and human beings, or their parts.

The rotation movements of existing systems are however always performed around the same central axis. As a consequence, these systems continue to suffer degradation of the spatial resolution in peripheral zones of the field of view due to the parallax error, even if this is minimized by methods of correction through DOI determination (e.g., AX-PET).

Through a PET system and respective acquisition method with two axes of rotation, the embodiments of the present invention aim to reduce even further the number of detectors required for the obtention of a PET image, while at the same time eliminate the parallax error and the need for determination of the DoI.

It is, therefore, one of the objectives of the present description the obtention of PET tomographic images in two or three dimensions, using one or more joined pairs of detectors which move together and execute two types of independent scans, around two axes of rotation, so as to cover a cylindrical field of view between the detectors, defined by the amplitude of one of the scans. The pairs of detectors are kept collinear and always aligned during all the scans, eliminating aberration effects due to the oblique penetration of the 511 keV photons in the scintillator crystals.

A system of positron emission tomography is described, characterized by comprising:
- two axes of rotation, wherein the first axis is fixed and the second axis is mobile within a circumference defined by the first axis and is mechanically coupled to a support plate;
- one or several pairs of scintillator crystals fixed to the support plate, each pair collinear and aligned along the same longitudinal axis;
- a photomultiplier coupled to each scintillator crystal;
- a support plate, fixed to the second axis of rotation, with a free region between the pair (or pairs) of scintillator crystals, region where the objects intended to be imaged are placed;
- a supply unit constituted by one or more DC-DC converters for polarization of one or more pairs of photomultipliers;
- an electronic system for readout of the signals from the photomultipliers constituted by individual circuits of amplification and circuits of coincidence detection between photomultipliers coupled to scintillator crystals of each pair;
- a controller unit constituted by one or more microcontrollers, for system control and communication between a computer and the remaining parts of the system above described.

An embodiment is characterized by having the first axis of rotation centred at half distance between the scintillator crystals of each pair and the second axis of rotation parallel and coincident with the frontal face of one of the scintillator crystals.

An embodiment is characterized by having the scintillator crystals coupled to the photomultipliers via optical gel or cement.

An embodiment is characterized by having all faces of each scintillator crystal except for the face coupled to the photomultiplier, coated with an optical reflective material.

An embodiment is characterized by having the pairs of scintillator crystals, the photomultipliers and respective supply unit and electronic readout system placed and integrated in the same support plate.

An embodiment is characterized by the acquisition of lines of response in different angular positions of the two rotation axes.

An embodiment is characterized by the alternate rotation of the two axes, wherein the first axis scans an angle of up to 360 degrees and, for each position of the first axis, the second axis scans an angle of up to 180 degrees that defines the field of view of the system.

An embodiment is characterized by the possible repetition of the alternate rotation of the two axes and for a predefined number of times.

An embodiment is characterized by the counting of the number of coincidences (lines of response) in each pair of scintillator crystals during predefined stoppage time at each position of the two axes.

An embodiment is characterized by the communication of the angular position of the two axes and of the number of coincidences in each stoppage position of the axes, from the controller unit to a computer, where the image is reconstructed in real time during acquisition.

A system of positron emission tomography for obtaining images of a subject is described, comprising:
- a first fixed axis of rotation;
- a second axis of rotation substantially parallel to the first axis, wherein the second axis is rotatable about the first axis at a predefined distance;
- an element of support rotatably coupled to the second axis;
- a pair of scintillators fixed to the element of support, said pair being collinear and aligned along a same longitudinal axis;
- two photomultipliers, each one optically coupled to one of the scintillators;
- wherein the element of support has a free region between the pair of scintillators for receiving the subject to be imaged.

In an embodiment, the element of support is a plate.

In an embodiment, the first axis is fixed to the same referential of the subject to be imaged.

In an embodiment, the second axis of rotation is parallel to the frontal face of one of scintillators.

In an embodiment, the second axis of rotation is coincident with the frontal face of one of the scintillators.

An embodiment comprises one or more additional pairs of scintillators fixed to the element of support, each pair being collinear and aligned along a same longitudinal axis, and respective photomultipliers, each one optically coupled to one of the scintillators.

An embodiment comprises a supply unit constituted by one or more DC-DC converters for polarization of one or more pairs of photomultipliers.

An embodiment comprises an electronic system for readout of the signals from the photomultipliers comprising individual circuits of amplification and circuits of coincidence detection between photomultipliers coupled to scintillators.

An embodiment comprises a controller unit comprising one or more microcontrollers for system control and communication between a computer and the remaining parts of the system.

In an embodiment, the first axis is positioned in the centre of the system.

In an embodiment, the first axis is substantially coincident with a line bisecting the distance between each scintillator of the pair of scintillators.

In an embodiment, the predefined distance at which the second axis is rotatable about the first axis is substantially equal to half of the distance between each of the scintillators of the pair of scintillators.

In an embodiment, the scintillators are coupled to the photomultipliers by optical gel or cement.

In an embodiment, all the faces of each scintillator crystal, except the face coupled to the photomultiplier, are coated with an optical reflective material.

In an embodiment, the pair or pairs of scintillators, photomultipliers and respective supply unit and electronic readout system are placed and integrated in the same support plate.

In an embodiment, the scintillators are scintillator crystals.

Further described is a method for acquisition of images of a subject by positron emission tomography, using a system according to any of the embodiments described, comprising acquiring lines of response, i.e., coincidences of signal between photomultipliers, in different angular positions of each one of the two rotation axes.

An embodiment comprises alternately rotating the two axes, wherein the first axis scans an angle of up to 360 degrees and, for each position of the first axis, the second axis scans an angle of up to 180 degrees, thus defining a field of view of the system.

An embodiment comprises repeating the alternate rotation of the two axes for a predefined number of times.

An embodiment comprises counting the number of lines of response, i.e., coincidences of signal between photomultipliers, in each pair of scintillators, for each position of the two axes of rotation.

In an embodiment, the coincidences are between opposing scintillators of the same pair or of different pairs.

An embodiment comprises communicating the angular position of each one of the two axes of rotation and the number of lines of response, i.e., coincidences of signal between photomultipliers, for each position of the two axes of rotation, from a controller unit to a computer, where the subject's image is reconstructed, preferentially in real time during said acquisition.

In an embodiment, the system counts the number of lines of response, i.e., coincidences of signal between photomultipliers, during a predefined stoppage time for each position of the two axes of rotation.

In an embodiment, the system counts the number of lines of response, i.e., coincidences of signal between photomultipliers, during a continuous movement of the two axes of rotation.

Further described is a non-transitory data storage medium comprising program instructions for implementing a system of acquisition of a subject's images by positron emission tomography, the programming instructions including instructions executable to carry out the method in any of the embodiments described.

BRIEF DESCRIPTION OF THE DRAWINGS

For an easier comprehension, figures are added in attachment, which represent preferential embodiments that do not intend to limit the object of the present description.

DETAILED DESCRIPTION

Figure 1:
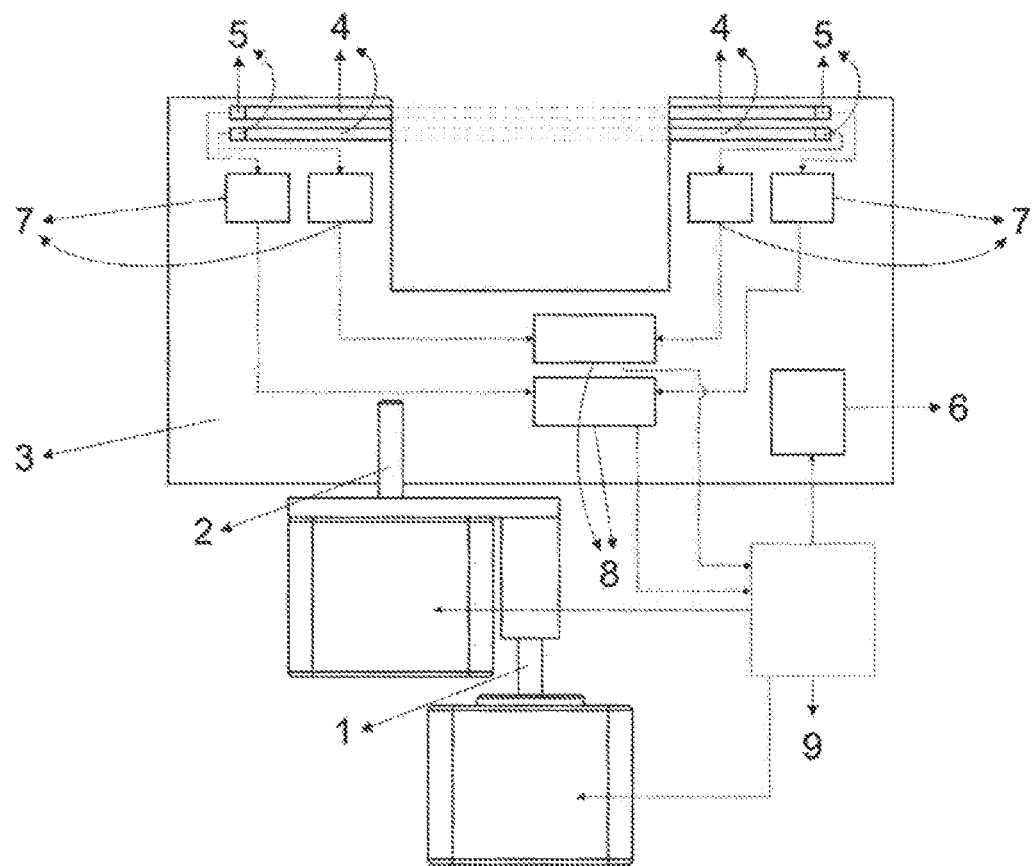
FIG. 1: Schematic representation of an embodiment of the PET system, constituted by two axes of rotation associated to two step motors, a support board with a free region between one or more (two, in this case) pairs of aligned scintillator crystals, each crystal coupled to a photomultiplier.

An embodiment of the system, whose schematics is represented in FIG. 1, comprehends:
- two axes of rotation 1 and 2, associated to two step motors or servo motors, in which axis 1 of the first motor is fixed, supports and rotates the second motor, whose axis 2 in its turn supports and causes a support board 3 to rotate;
- one support board 3, fixed to the mobile axis of rotation 2, containing one or more pairs of aligned and collinear scintillation detectors, and presenting a free region between the pairs of detectors where the objects intended to be imaged are placed;
- one or more pairs of scintillation detectors, each detector constituted by a scintillator crystal (4) optically coupled to a photomultiplier 5;
- one supply unit constituted by one or more DC-DC converters 6 for polarization of the photomultipliers 5;
- an electronic system for readout of the signals from the detectors constituted by amplifying circuits 7 of the individual detectors and coincidence detection circuits 8 between the detectors of each pair, which can be integrated in the support board 3;
- a controller unit 9 constituted by one or more microcontrollers, for system control and communication between a computer and the remaining parts of the system above described.

Figure 2:
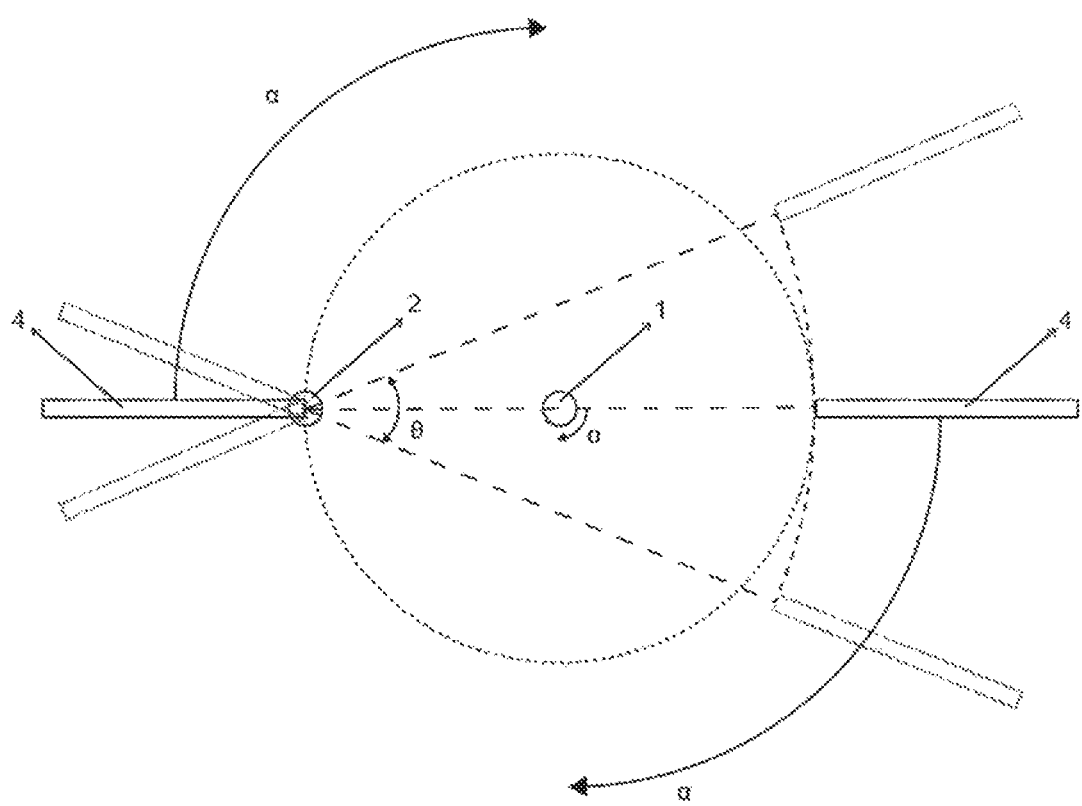
FIG. 2: Schematic representation of an embodiment of the method of PET image acquisition with two axes of rotation, in which one axis is fixed and the other is mobile within a circumference centred in the first axis, in order to acquire several lines of response covering a field of view between detectors.

An embodiment refers also to the method of PET image acquisition, which consists of:
- acquisition of lines of response in different angular position of two rotation axes 1 and 2, in which axis 1 is fixed and is centred at half distance between the detectors of each pair and axis 2 is mobile within circumference defined by axis 1 and is parallel and coincident with the frontal face of one of the scintillator crystals, as illustrated in FIG. 2;
- alternate rotation of the two axes 1 and 2, in which axis 1 scans an angle α of up to 360 degrees and, for each angular position of axis 1, axis 2 scans an angle θ of up to 180 degrees that defines the field of view of the system, as illustrated in FIG. 2;
- count of the number of coincidences in each pair of detectors during the stoppage time at each position of the two axes 1 and 2, wherein each coincidence corresponds to the obtention of simultaneous signals from the two photomultipliers 5 of each pair of detectors, with amplitudes above a certain value X after passage through amplifying circuit 7 and during a time window of length T, with X and T defined by the coincidence detection circuit 8;
- communication of the angular position of the two axes 1 and 2 and of the number of coincidences (lines of response) in each position, from the controller unit 9 to the computer, where image is reconstructed in real time during acquisition.

FIG. 1 shows an embodiment of the scheme of the PET system, constituted by two axes of rotation 1 and 2 associated to two step motors, a support board 3 with a free region between one or more (two, in this case) pairs of aligned scintillator crystals 4, each crystal coupled to a photomultiplier 5 with respective DC-DC converters 6 for a polarization circuit, an electronic system for readout of signals from the photomultipliers 5 and coincidence detection circuits 8 between crystals of each pair, and a controller unit 9 which serves as communication interface between computer and different parts of the system.

FIG. 2 shows the schematics of an embodiment of the method of PET image acquisition with two axes of rotation 1 and 2, in which axis 1 is fixed and axis 2 is mobile within circumference defined by axis 1, $\alpha$ represents the angle scanned by axis 1 and $\theta$ represents the angle scanned by axis 2 for each angular position of axis 1. The two axes are used to move one or more pairs of scintillator crystals 4 in order to acquire lines of response covering a cylindrical field of view between the detectors.

The term "comprises" or "comprising" when used in this document is destined to indicate the presence of characteristics, elements, integers, steps and components mentioned, but does not prevent the presence or the addition of one or more other characteristics, elements, integers, steps and components, or groups of the same.

The embodiments described are combinable between them.

The present invention is not, naturally, in any way restricted to the embodiments described in this document and a person with average knowledge of the area may foresee many possibilities of its modification and of substitutions of technical characteristics by other equivalent ones, depending on the requirements of each situation, as defined in the appended claims.

The following claims additionally define embodiments of the disclosure.

The invention claimed is:

1. System of positron emission tomography for obtaining images of a subject, comprising:
    a first fixed axis of rotation;
    a second axis of rotation substantially parallel to the first fixed axis of rotation, wherein the second axis of rotation is rotatable about the first fixed axis of rotation at a predefined distance;
    an element of support rotatably coupled to the second axis of rotation;
    a pair of scintillators fixed to the element of support, said pair of scintillators and said element of support being collinear and aligned along a same longitudinal axis;
    two photomultipliers, each one optically coupled to one scintillator of the pair of scintillators;
    wherein the element of support has a free region between the pair of scintillators for receiving the subject to be imaged.

2. System according to claim 1 wherein the element of support is a plate.

3. System according to claim 1 wherein the first fixed axis of rotation is fixed to the same referential of the subject to be imaged.

4. System according to claim 1 wherein the second axis of rotation is parallel to a frontal face of one of the pair of scintillators.

5. System according to claim 1 wherein the second axis of rotation is coincident with a frontal face of one scintillator of the pair of scintillators.

6. System according to claim 1 comprising one or more additional pairs of scintillators fixed to the element of support, each additional pair of scintillators being collinear and aligned along a same longitudinal axis, and respective photomultipliers, each one optically coupled to one of the additional pair of scintillators.

7. System according to claim 1 comprising an electronic system for readout of signals from the photomultipliers comprising individual amplifying circuits and coincidence detection circuits between the photomultipliers coupled to the pair of scintillators.

8. System according to claim 1 wherein the first fixed axis of rotation is substantially coincident with a line bisecting the distance between each of the scintillators of the pair of scintillators.

9. System according to claim 1 wherein the predefined distance at which the second axis of rotation is rotatable about the first fixed axis of rotation is substantially equal to half of the distance between each of the scintillators of the pair of scintillators.

10. System according to claim 1 wherein the pair or pairs of scintillators, photomultipliers and a respective supply unit and electronic readout system are placed and integrated in the same support plate.

11. System according to claim 1 wherein the scintillators are scintillator crystals.

12. Method of acquisition of images of a subject by positron emission tomography using a system according to claim 1, comprising acquiring lines of response, in the form of coincidences of signal between the photomultipliers, in different angular positions of each one of the first fixed axis of rotation and the second axis of rotation.

13. Method according to claim 12, comprising alternately rotating the first fixed axis of rotation and the second axis of rotation, wherein the first fixed axis of rotation scans an angle of up to 360 degrees and, for each position of the first fixed axis of rotation the second axis of rotation scans an angle of up to 180 degrees, to define a field of view of up to 180 degrees as scanned by the second axis of rotation, said field of view being rotatable by 360 degrees about the first axis of rotation.

14. Method according to claim 12, comprising repeating the alternate rotation of the first fixed axis of rotation and the second axis of rotation for a predefined number of times.

15. Method according to claim 12, comprising counting the number of lines of response in each pair of scintillators, for each position of the first fixed axis of rotation and the second axis of rotation.

16. Method according to claim 15 wherein the coincidences are between opposing scintillators of the same pair or of different pairs of scintillators.

17. Method according to claim 12, comprising communicating the angular position of each one of the first fixed axis of rotation and second axis of rotation and the number of lines of response for each position of the first fixed axis of rotation and the second axis of rotation, from a controller unit to a computer, where the image of the subject is reconstructed, preferentially in real time during said acquisition.

18. Method according to claim 12, wherein the system counts the number of lines of response during a predefined stoppage time for each position of the first fixed axis of rotation and the second axis of rotation.

19. Method according to claim 12, wherein the system counts the number of lines of response during a continuous movement of the first fixed axis of rotation and the second axis of rotation.

20. Non-transitory data storage medium comprising program instructions for implementing a system of acquisition of a subject's images by positron emission tomography, the program instructions including instructions executable to carry out the method of claim 12.

* * * * *